United States Patent
El-Hajal et al.

(10) Patent No.: US 10,620,454 B2
(45) Date of Patent: Apr. 14, 2020

(54) SYSTEM AND METHOD OF OBTAINING FIT AND FABRICATION MEASUREMENTS FOR EYEGLASSES USING SIMULTANEOUS LOCALIZATION AND MAPPING OF CAMERA IMAGES

(71) Applicant: Optikam Tech, Inc., Montreal (CA)

(72) Inventors: Bassem El-Hajal, Montreal (CA); Marco Lancione, Montreal (CA); Piotr Szymborski, Montreal (CA)

(73) Assignee: Optikam Tech, Inc. (CA)

(*) Notice: Subject to any disclaimer, the term of this patent is extended or adjusted under 35 U.S.C. 154(b) by 230 days.

(21) Appl. No.: 15/853,703

(22) Filed: Dec. 22, 2017

(65) Prior Publication Data

US 2019/0196221 A1    Jun. 27, 2019

(51) Int. Cl.
| | |
|---|---|
| *G02C 7/02* | (2006.01) |
| *G02C 13/00* | (2006.01) |
| *G06T 19/00* | (2011.01) |
| *G06T 7/593* | (2017.01) |
| *A61B 3/00* | (2006.01) |
| *A61B 3/04* | (2006.01) |

(52) U.S. Cl.
CPC ............... *G02C 7/027* (2013.01); *A61B 3/00* (2013.01); *G02C 13/003* (2013.01); *G02C 13/005* (2013.01); *G06T 7/593* (2017.01); *G06T 19/006* (2013.01); *A61B 3/04* (2013.01); *G02C 7/028* (2013.01); *G06T 2207/10021* (2013.01); *G06T 2207/30201* (2013.01)

(58) Field of Classification Search
CPC ...... G02C 7/027; G02C 13/003; G06T 19/006
USPC ..................................................... 351/159.75
See application file for complete search history.

(56) References Cited

U.S. PATENT DOCUMENTS

| | | | |
|---|---|---|---|
| 5,983,201 A | 11/1999 | Fay | |
| 6,142,628 A | 11/2000 | Saigo | |
| 7,016,824 B2 | 3/2006 | Waupotitsch | |
| 7,434,931 B2 | 10/2008 | Warden et al. | |
| 8,733,936 B1 | 5/2014 | Kornilov | |
| 9,665,984 B2 | 5/2017 | Ye et al. | |
| 2011/0102553 A1 | 5/2011 | Corcoran et al. | |
| 2013/0063566 A1 | 3/2013 | Morgan-Mar et al. | |
| 2013/0088490 A1 | 4/2013 | Rasmussen et al. | |
| 2013/0321763 A1* | 12/2013 | Haddadi .............. | G02C 13/005 351/204 |
| 2014/0104568 A1 | 4/2014 | Cuta et al. | |

(Continued)

*Primary Examiner* — James R Greece
(74) *Attorney, Agent, or Firm* — LaMorte & Associates, P.C.

(57) ABSTRACT

A system and method for determining the measurements needed to fabricate prescription eyeglasses. A person is imaged wearing the eyeglass frames, from a first camera position and a subsequent camera position. This produces images having differing perspectives from known distances. Common measurement points are identified within at least some of the images. The common measurement points undergo positional changes between the images having said differing perspectives. The positional changes of the common measurement points and the known distance to the imaging camera are utilized to map three dimensional coordinates for the measurement points using an actual measurement scale. Fabrication measurements are calculated between the various three-dimensional coordinates in the same scale.

19 Claims, 7 Drawing Sheets

(56) References Cited

U.S. PATENT DOCUMENTS

2015/0009207 A1 1/2015 Guo et al.
2015/0055085 A1* 2/2015 Fonte .................. G06F 17/50
                                                     351/178
2015/0055086 A1 2/2015 Fonte et al.

* cited by examiner

SYSTEM AND METHOD OF OBTAINING FIT AND FABRICATION MEASUREMENTS FOR EYEGLASSES USING SIMULTANEOUS LOCALIZATION AND MAPPING OF CAMERA IMAGES

BACKGROUND OF THE INVENTION

1. Field of the Invention

In general, the present invention relates to measurement systems and methods that are used to properly fit prescription eyewear. More particularly, the present invention relates to systems and methods that obtain measurements from camera images for fitting prescription eyewear.

2. Prior Art Description

Only a few decades ago, cameras were dedicated devices. That is, the camera had no other function but to take pictures. The camera had an objective lens that had to be pointed toward the object that was being imaged. The objective lens then had to be manually focused on that object. As technology progressed, cameras were developed that had the ability to focus automatically. Using an integrated autofocus system, the camera would automatically focus on a targeted object in front of the camera. Autofocusing was typically accomplished using a time of flight system. In a time of flight system, an emitter, such as an infrared light source, would shine a beam of light in the direction that the camera lens was pointed. The light would then travel to the object and be reflected back toward the camera. The camera also contained a sensor that could capture the reflected light in the frequency range used by the emitter. By sensing the time of flight of the emitted energy between transmission and reception, the distance of the object could be calculated. This information was then used to automatically focus the lens of the camera.

Cameras that most people use today are not dedicated devices. Rather, cameras have been integrated into handheld smart phones and other such electronic devices. As such, any person who carries a smart phone, also carries a camera. Cameras used on smart phones have small objective lenses. Furthermore, these objective lenses cannot be manually focused. As such, cameras on smart phones must rely upon autofocus systems to capture clear images.

Although time of travel systems can still be used to determine the distance an object is from the camera, more useful information is typically obtained using depth mapping. In a smart phone, basic depth mapping is commonly achieved using a structured light system. In a structured light system, a known light pattern such as a grid is projected onto an object in front of the camera. This is typically accomplished using infrared light that is not visible to the naked eye. The projected grid will be distorted by the shape of the object it hits. Using the processing power available within a smart phone, the distortions in the grid can be converted into a depth map that represents the shape of the targeted object. A depth map is a map of per-pixel data containing depth-related information. A depth map contains data useful for conversion methods, focusing, and camera calibration to aid in various computer vision tasks.

Some smart phones have two cameras that are set into a stereoscopic pair. Depth mapping can be easily achieved using stereoscopic cameras by comparing the left/right images and calculating the distance between an object and the cameras. However, most smart phones only have a single camera or a single camera on the screen side of the smartphone that is used to take selfies. Obtaining an accurate depth map from a single camera point is more complex. With a single camera, a time of travel system or a structured light system is used to obtain depth data regarding a single image. A disparity map is then generated by comparing normalized shift values in successive images. In many modern smart phones, disparity maps are generated using a simultaneous localization and mapping (SLAM) system. SLAM systems track a set of targeted pixel points through successive camera frames and using these tracks to triangulate a value for position in real space. Simultaneously, the estimated positions in real space are used to calculate the camera position which could have observed them.

When the camera of a smart phone is turned on, it does not have two different images with which to calculate distances. However, once two images are taken in succession, data becomes available. Furthermore, additional data can be obtained from the smart phone using the accelerometer sensors of the smart phone that can be used to estimate changes in camera position between the first image and a subsequent image. Accordingly, the optical differences between subsequent images becomes known as well as the corresponding differences in the position and aim of the camera on the smart phone. Aside from doing the triangulation on each of the targeted features in the subsequent images, the SLAM system also does a comparison between the differences in each feature's relationship to other features in the image. The result is that the smart phone has two different views of the target object, it knows the approximate angles of focus, it knows the distance between the lens positions, and it tracks known features and their relationship to each other. From this, the smart phone can get a very good approximation of how each feature is positioned in real space with relation to the other features, essentially producing a three-dimensional mapping of targeted points in the observed space.

When using a SLAM system to generate a three-dimensional mapping of space, one crucial difficulty is the issue of scale. Scale is the relationship between actual distance between targeted points in real space and the apparent distance between points in a three-dimensional mapping. Most smart phones only have one camera. Real scale cannot be directly measured using a single camera. This means that the resulting three-dimensional mapping is only correct relative to an unknown scale factor. A poorly constrained scale can introduce inconsistency in the map over time. Creating a map like this is commonly referred to as dimensionless mapping, because there is no real-world dimension or meaning attached to the distances between points on the map. Within the three-dimensional mapping, the units of measure can be anything. As such, a SLAM system may be able to determine the shape of a car, but it cannot determine if it is imaging a toy car or a real car due to lack of scale.

A sense of scale can be applied to a three-dimensional map created by a SLAM system by simply imaging some object of a known size. However, in many applications, such a solution is not available. For example, suppose a person is using a smartphone to image their own face in a selfie. Points on the face can be modeled, but the dimensions between points are unknown. Accordingly, any such three-dimensional map is not very useful in measuring anatomical features of the face.

In U.S. Pat. No. 9,665,984 to Ye and U.S. Pat. No. 7,016,824 to Waupotitsch, images of the face are used to create virtual 3D models of the face. These models are used to demonstrate how various styles of eyeglass frames would look on the face. However, due to scale issues, the detailed measurements needed to properly fit the eyeglasses properly to the face cannot be obtained.

Eyeglasses are fabricated in a manner that takes into account both the style of the selected eyeglass frames and the anatomical features of the person who will wear the eyeglass frames. To properly fit eyeglasses, several measurements must be made in order to ensure that the prescription lenses are fabricated properly. Some measurements depend solely upon the style and model of the eyeglass frames being considered. However, many other measurements depend upon the anatomy of the person being fitted and how the eyeglass frames sit upon the face when being worn. For instance, the distance between a person's eyes varies from person to person. Furthermore, the shape and slant of a person's nose varies from person to person. The size and slant of the nose determines how far down the face a set of eyeglass frames will come to rest in front of the eyes. The position of the head and the posture of the body also have significant effects on the proper fitting of eyeglasses. These variables and others should be measured to properly fit eyeglasses and to correctly fabricate lenses for those eyeglasses.

In U.S. Pat. No. 8,733,936 to Kornilou, a system is disclosed where measurements are attempted to be taken directly from a 3D model. However, in order to provide effective scaling, the person being fitted with the eyeglasses must first be imaged holding a measurement scale near his/her face. This may be practical for a person sitting in an optician's office. However, the need to hold a scale near the face is not practical in many situations, such as when a person is taking a selfie with his/her own smart phone.

A need therefore exists for a system and method that can be used to image a person wearing glasses using a smart phone camera in a manner that does not require showing a scale in the image, yet wherein the image can be used to generate the measurements needed to accurately fabricate a set of eyeglasses. This need is met by the present invention as described and claimed below.

SUMMARY OF THE INVENTION

The present invention is a system and method for determining the measurements needed by a lens fabricator to correctly fit prescription eyeglasses to an individual. The system and method take into account how the frames fit naturally on the head and how the person's posture orients the head and alters the line of sight through the lens of the eyeglasses. The person first selects eyeglass frames into which the prescription lenses are to be set. The person wears the eyeglass frames. The person is imaged wearing the eyeglass frames, from a first camera position and from at least one subsequent camera position. This produces images having differing perspectives, wherein the first camera position and the subsequent camera position are at known distances from the person when the images are taken. These distances are known from the autofocus system of the camera.

Common measurement points are identified within at least some of the images. At least some of the common measurement points undergo positional changes between the images having said differing perspectives. The positional changes of the common measurement points and the know distance to the imaging camera are utilized to map three dimensional coordinates for the measurement points using an actual measurement scale.

Fabrication measurements are calculated between the various three-dimensional coordinates in the same scale. The fabrication measurements can then be used to fabricate prescription lenses.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention system and method can be used to check the fit of eyeglass frames and to determine the measurements needed to accurately fabricate prescription lenses for the frames. The frames and lenses can be used to form eyeglasses, sunglasses, or safety glasses. Only one exemplary embodiment of present invention system and method is illustrated. This embodiment is exemplary and is intended to represent one of the best modes contemplated for the invention. The exemplary embodiment, however, is used for the purpose of explanation only and should not be considered a limitation when interpreting of the appended claims.

Figure 1:
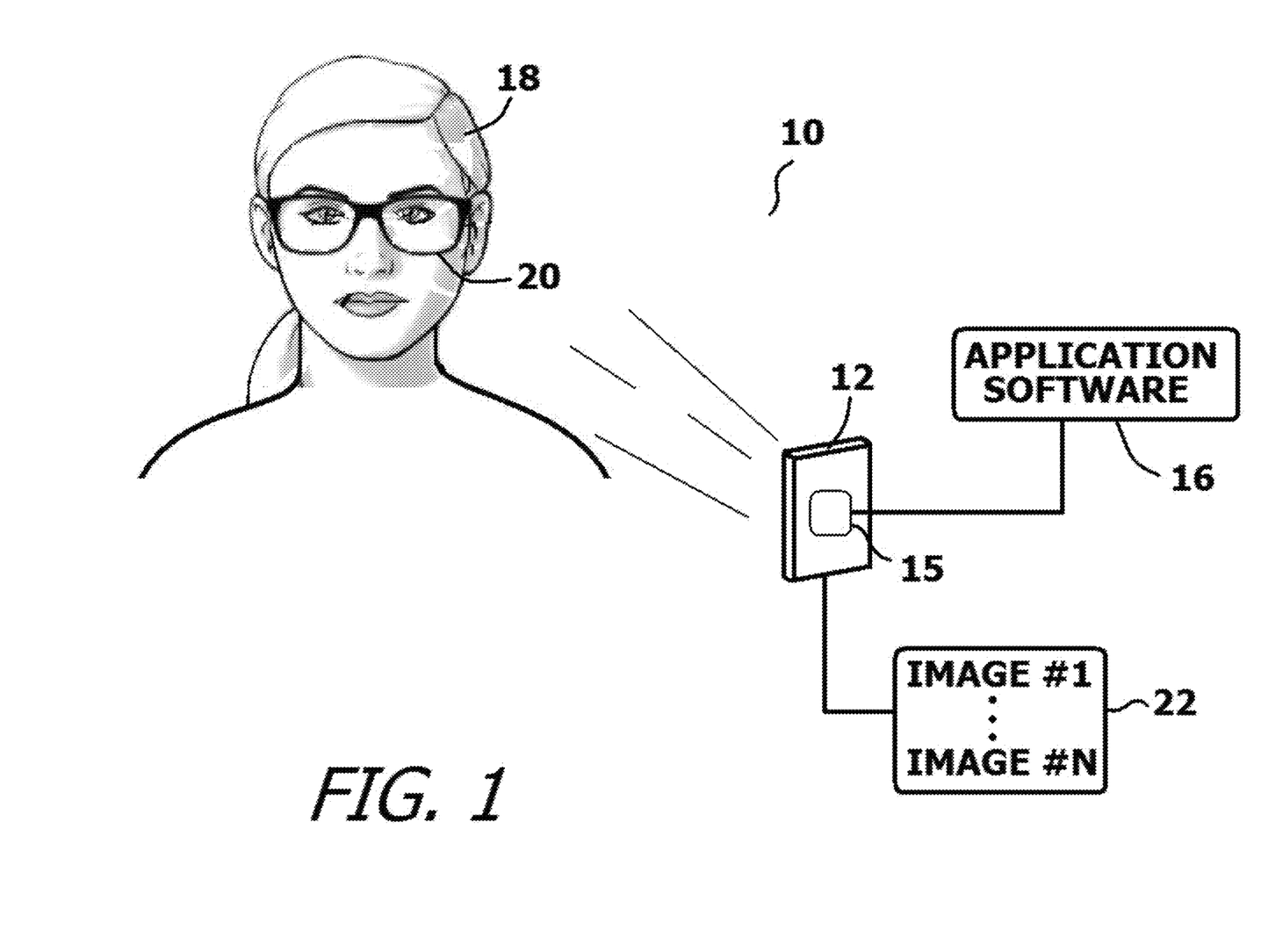
FIG. 1 shows the hardware of the present invention system imaging a person from the front.
Figure 2:
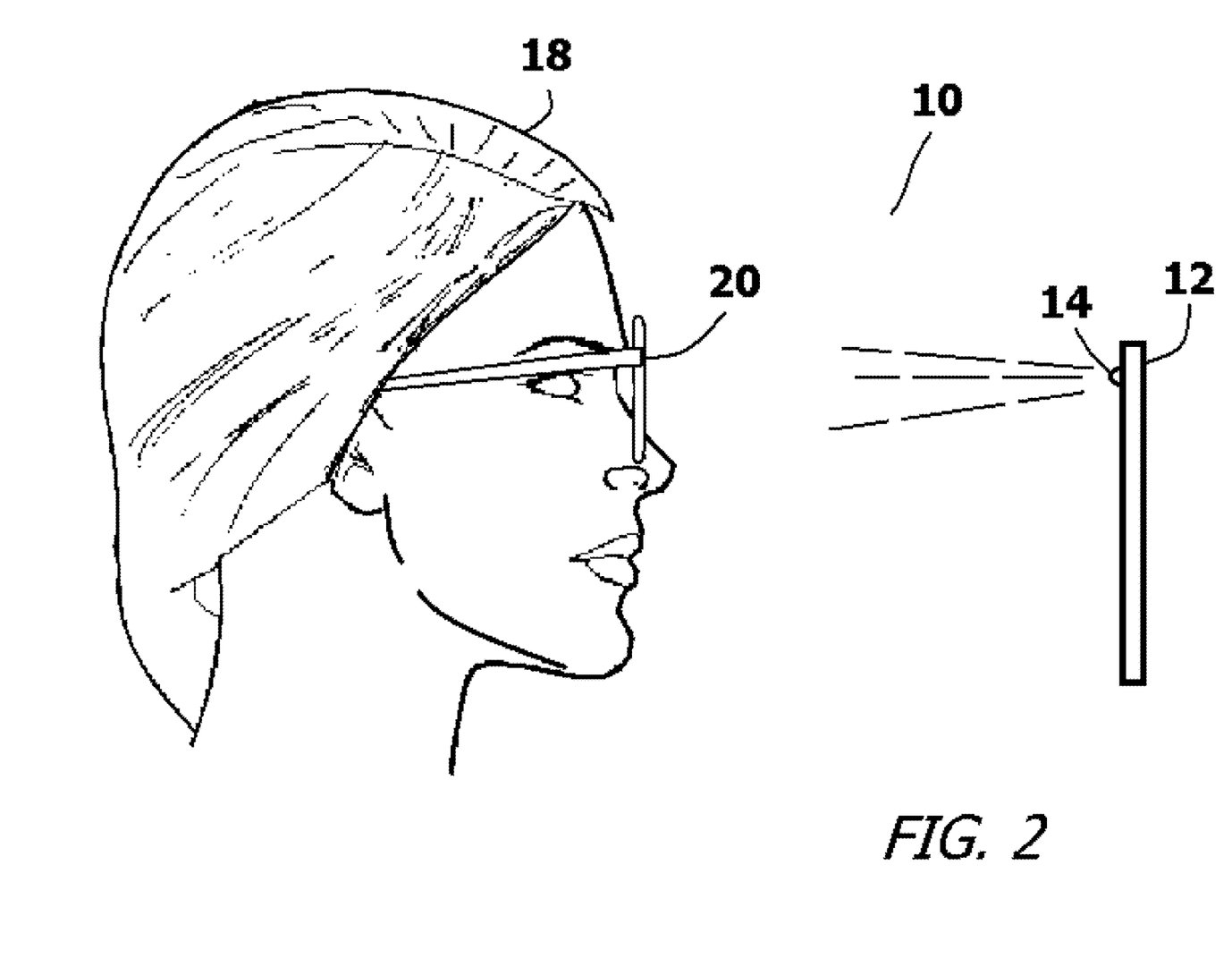
FIG. 2 shows the hardware of the present invention system imaging a person from the side.

As will be explained, the purpose of the present invention is to provide a way to check the fit of eyeglass frames and to obtain many of the measurements needed to create prescription lenses for the frames by simply imaging a person using a smartphone or tablet computer. Referring to FIG. 1 and FIG. 2, the components and the environment of a measurement system 10 is shown in accordance with the present invention. The measurement system 10 requires the use of a smartphone 12 or similar handheld electronic device that has an integrated camera 14. The smartphone 12 has a processor 15 that runs application software 16 that causes the smartphone 12 to perform the operational functions that are described below.

The smartphone 12 is used to image a person 18 wearing eyeglass frames 20. The eyeglass frames 20 can be a set that the person 18 already owns and likes. Alternatively, the eyeglass frames 20 can be a set that the person 18 is trying on in a store or in an optician's office. Regardless of the origin of the eyeglass frames 20, the person 18 desires to see how those eyeglass frames 20 look on the face. In addition to accomplishing this task, the measurement system 10 also calculates many of the measurements needed to properly fabricate prescription lenses for the eyeglass frames 20.

The person 18 selects a set of eyeglass frames 20 and wears those eyeglass frames 20 in a comfortable manner. It does not matter if the eyeglass frames 20 contain lenses. It is just the look and the fit of the eyeglass frames 20 on the person 18 that is at issue.

If the person 18 likes the way the eyeglass frames 20 feel while being worn, the person 18 is then imaged using a smartphone 12. The images 22 taken of the person 18 can be a selfie, wherein the person 18 takes his/her own images. Alternatively, the images 22 can be taken by another person, such as an optician. More than one image is taken. An initial image is taken with the camera 14 in a first location, and at least one other subsequent image is taken with the camera 14 in a different location. Accordingly, each of the images 22 has a different perspective.

When each of the images 22 is taken, the image 22 is autofocused using the autofocus feature designed into the smartphone 12. That is, the smartphone 12 uses an integrated time of travel system and/or a structured light system to focus the camera 14. The data generated by the autofocus system is used to focus the camera 14 by accurately determining how far the camera 14 is from features on the person's face. This is especially true if the camera 14 is held at arm's length, as with a selfie. With the camera 14 being held less than one meter from the face, the face dominates the field of view and the camera 14 can accurately determine the distances between the camera 14 and the various features of the face in real scale. Accordingly, it will be understood that for each of the images 22 of the person 18 taken by the smartphone 12, the distance from the camera 14 to various facial features are known scaled variables.

The images 22 taken by the smartphone 12 may be posed. However, it is preferred that the images 22 of the person 18 be taken while the person 18 is wearing the eyeglass frames 20 in a natural manner. The person 18 is instructed to wear the eyeglass frames 20 in a comfortable position. The person 18 may then be asked to recreate a common situational simulation. If the person 18 typically wears eyeglasses when sitting at a desk, then the person 18 is asked to sit at a desk. If the person 18 typically wears eyeglasses when walking, then the person 18 is asked to walk. Similar situational simulations can be practiced for other activities, such as standing, reading, driving and the like. What is of importance is that the person 18 wears the eyeglass frames 20 in the same manner as they would in real life. Likewise, it is important that the person 18 places his/her body in the same positions and holds his/her head in the same manner as he/she would in everyday life. Accordingly, the overall orientation of the eyeglass frames 20 is true to everyday life.

The smartphone 12 is used to take images 22 as the person 18 simulates common day-to-day activities. Alternatively, a person can take a selfie while actually performing some day-to-day activities. Once the images 22 are taken with the camera 12, the person 18 can simply look at the images 22 recorded by the smartphone 12 to determine if he/she likes the look of the eyeglass frames 20. In addition, there are also commercially available software applications that can be run by a smartphone 12 that can integrate the images 22 into a virtual 3D model. Such software can be run on the smartphone 12 so that the person 18 can assess the aesthetics of the eyeglass frames 20.

Figure 3:
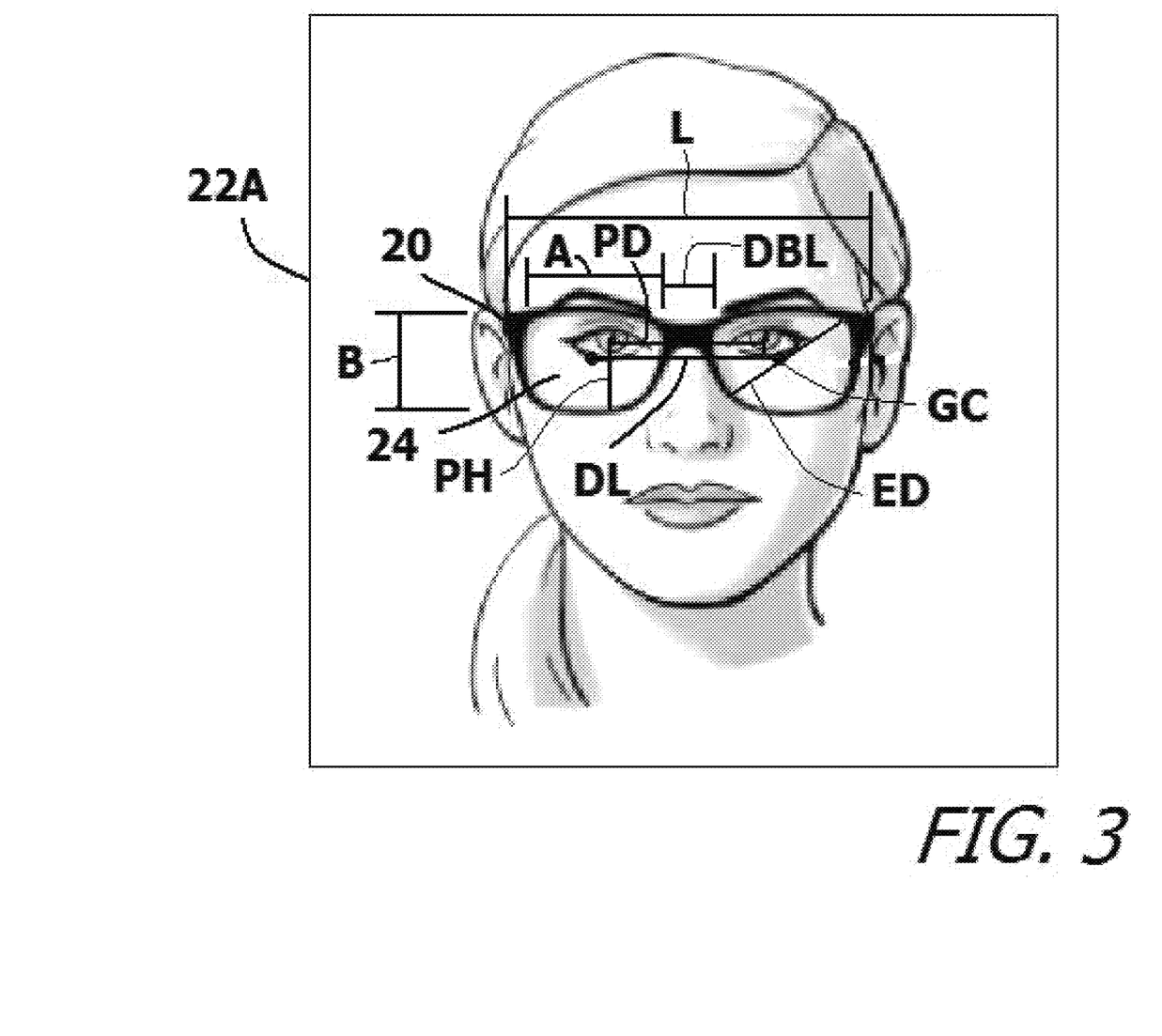
FIG. 3 is a front image of an individual wearing eyeglass frames, wherein the image indicates the variables needed to be known for the proper fabrication of prescription lenses.
Figure 4:
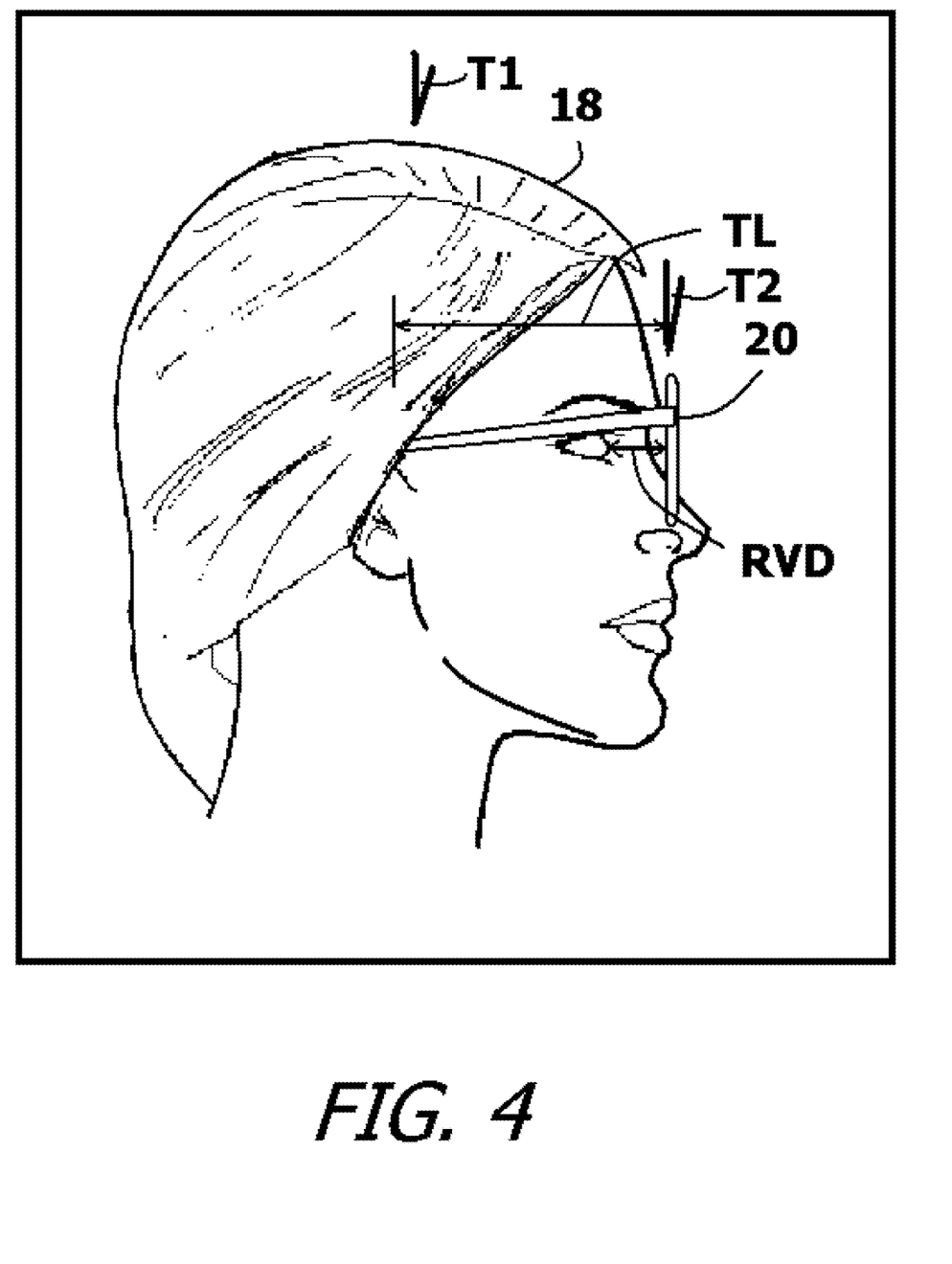
FIG. 4 is a side view of an individual wearing eyeglass frames and indicating some variables needed for the proper fabrication of prescription lenses.

FIG. 3 and FIG. 4 in conjunction with FIG. 1 illustrate two exemplary images 22A, 22B that are obtained using the camera 14 on the smartphone 12. In order to properly fabricate a set of prescription lenses 24 for a selected set of eyeglass frames 20, the physical dimensions of the eyeglass frames 20 must be known. In addition, certain measurements must be taken from the eyeglass frames 20 that reference the anatomy of the eyes and face. Collectively, all the major variables that are needed to properly fabricate a set of prescription eyeglasses are present in Table 1, below.

TABLE 1

| Frame Dimension Variables | |
| --- | --- |
| A | Lens Length |
| B | Lens Height |
| ED | Effective Diameter |
| GC | Geometrical Centers |
| DL | Datum Line |
| L | Frame Length |
| DBL | Distance Between Lenses |
| Anatomical Dependent Variables | |
| PH | Pupil Height |
| PD | Pupil Distance |
| PTA | Pantoscopic Tilt Angle |
| RVD | Rear Vertex Distance |

FIG. 3 is a front image 22A of a person wearing eyeglass frames 20. FIG. 4 is a side image 22B of the same. The eyeglass frames 20 have lens openings which are designed to hold prescription lenses 24. Referring to Table 1 in conjunction with FIG. 3 and FIG. 4, it will be understood that each model and style of eyeglass frames 20 has its own critical dimensions that must be known in order to shape the prescription lenses 24 for those eyeglass frames 20. The measurement variables include the overall shape of the eyeglass frames 20. Eyeglass frames 20 hold the prescription lenses 24 in a lens plane. Typically, the lens plane associated with a set of eyeglasses frames is at a slight angle relative to the vertical. This tilt angle T2 is sometimes referred to as the "device panto" in the industry. The tilt of the lens plane is also affected by the tilt angle T1 of the person's head. This tilt angle T1 is caused by posture and the way the person 18 holds his/her head.

Within the overall shape of the eyeglass frames 20, there are the lens width "A" and the lens height "B". There is the effective diameter "ED" as measured through the geometric center "GC" of each prescription lens 24. The geometric centers "GC" of both lenses 24 align horizontally on the datum line "DL". The frame length "L" is the distance between temples in the horizontal plane. The bridge size, or distance between lenses 24 "DBL" is the minimum distance between the left and right lenses 24. The pantoscopic tilt angle "PTA" corresponds to the total tilt of the lens plane. The proper pantoscopic tilt angle "PTA" for the person 18 is highly dependent upon the natural head posture of that person 18. This is because the vertical plane is a constant and any downward tilt of the head directly changes the tilt of the eyeglasses frames 20 relative the vertical plane. As such, the pantoscopic tilt angle "PTA" is the sum of the tilt angle T2 caused by the device panto plus the tilt angle T1 cause by head posture.

Other measurements that depend upon the anatomy of the person 18 wearing the eyeglass frames 20 include pupil height "PH", pupil distance "PD", and rear vertex distance "RVD". The pupil height "PH" is the measured height of the pupils above the bottom of the prescription lenses 24. The pupil distance "PD" is the distance between pupils in the horizontal plane. The rear vertex distance "RVD" is the gap distance between the pupil and the prescription lenses 24. The pantoscopic tilt angle "PTA", pupil height "PH" and the rear vertex distance "RVD" are measurements that depend upon how the prescription lens 24 are held in front of the eyes. They also depend upon how the person 18 normally orients his/her head when looking through the prescription lens 24.

If a person has a slight slouch or downward head inclination, the tilt angle T1 affects the overall pantoscopic tilt angle "PTA" of the eyeglass frames 20 when worn. Variations to the pantoscopic tilt angle "PTA", can also affect pupil height "PH" and rear vertex distance "RVD". All three affect the line of sight through the prescription lenses 24.

Figure 5:
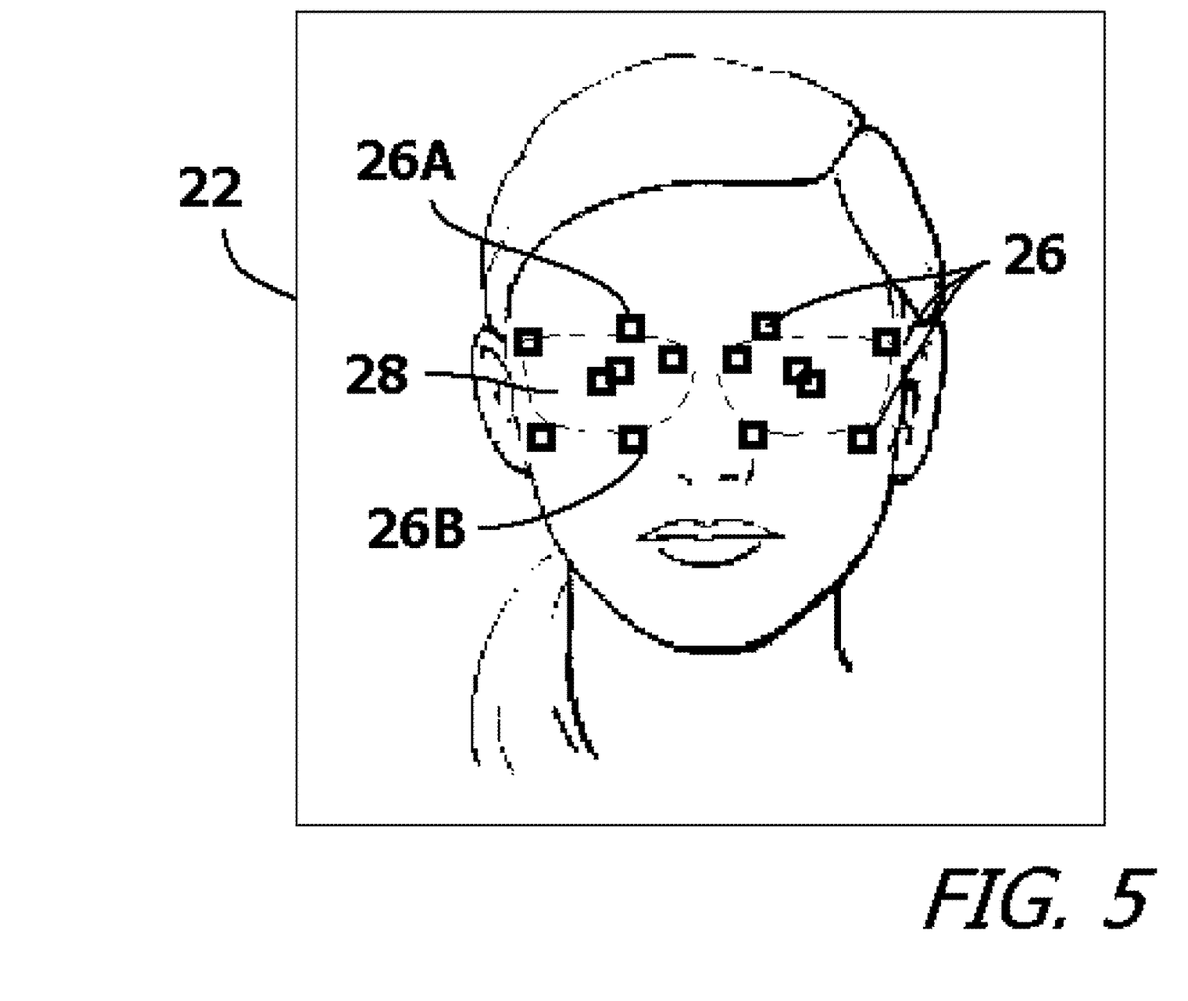
FIG. 5 shows exemplary measurement points selected on a front image.
Figure 6:
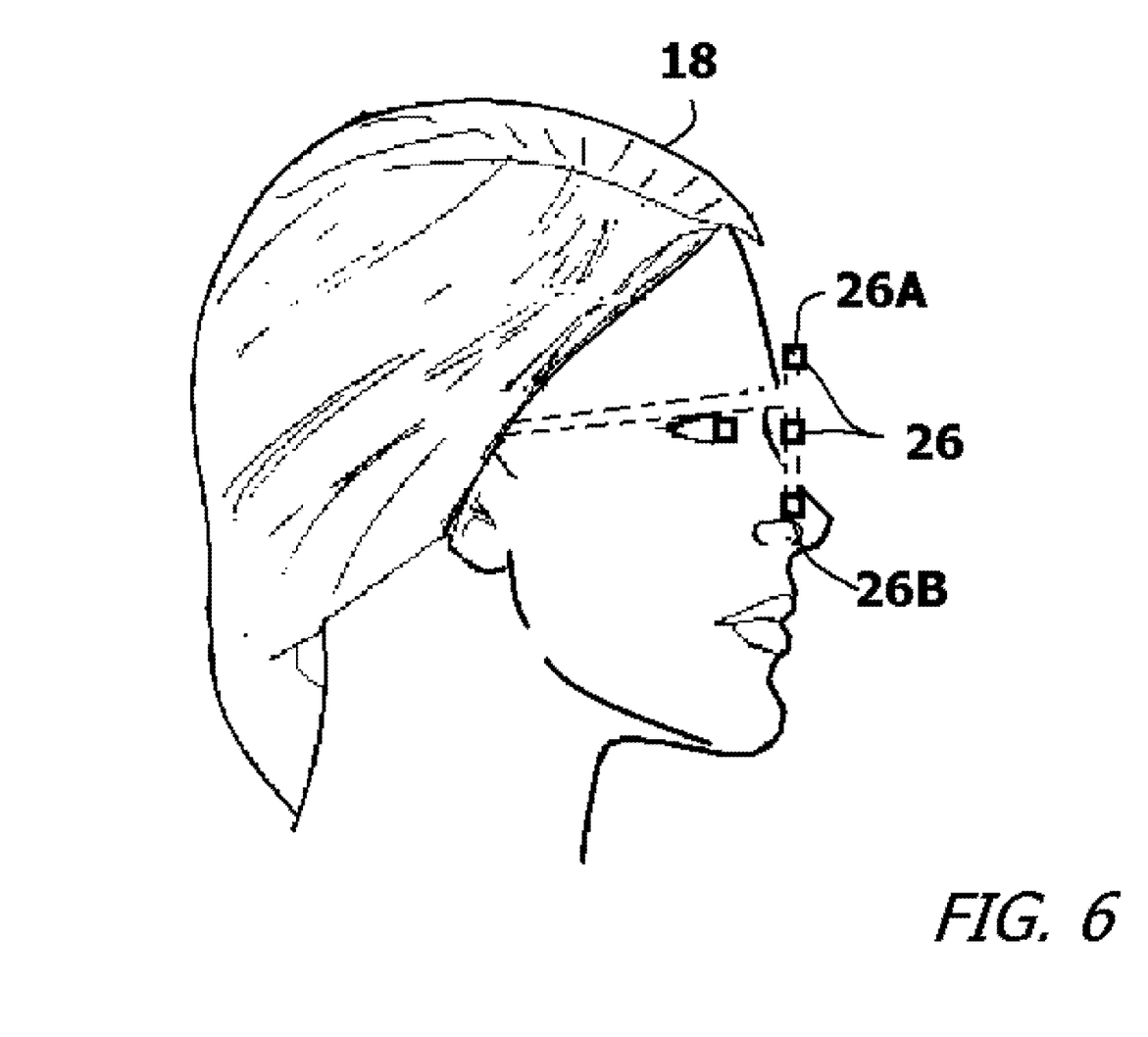
FIG. 6 shows exemplary measurement points selected on a side image.

Referring to FIG. 5 and FIG. 6 in conjunction with FIG. 1, it will be understood that the images 22 taken of the person 18 can be viewed on the smartphone 12. Using the application software 16, a user can identify specific critical measurement points 26 in the images 22. The measurement points 26 correspond to end points between where measurements are typically taken. For example, in order to measure the lens height "B", measurement points 26A, 26B have to be identified on opposite points of the lens window 28. Some of the measurement points 26, such as the centers of the eyes and the ends of the eyeglass frames 20 may be automatically identified with imaging software. However, due to the large disparity in eyeglass frame shapes, faces shapes, frame colors and skin color, some human input is needed to ensure all the important measurement points 26 are identified.

Figure 7:
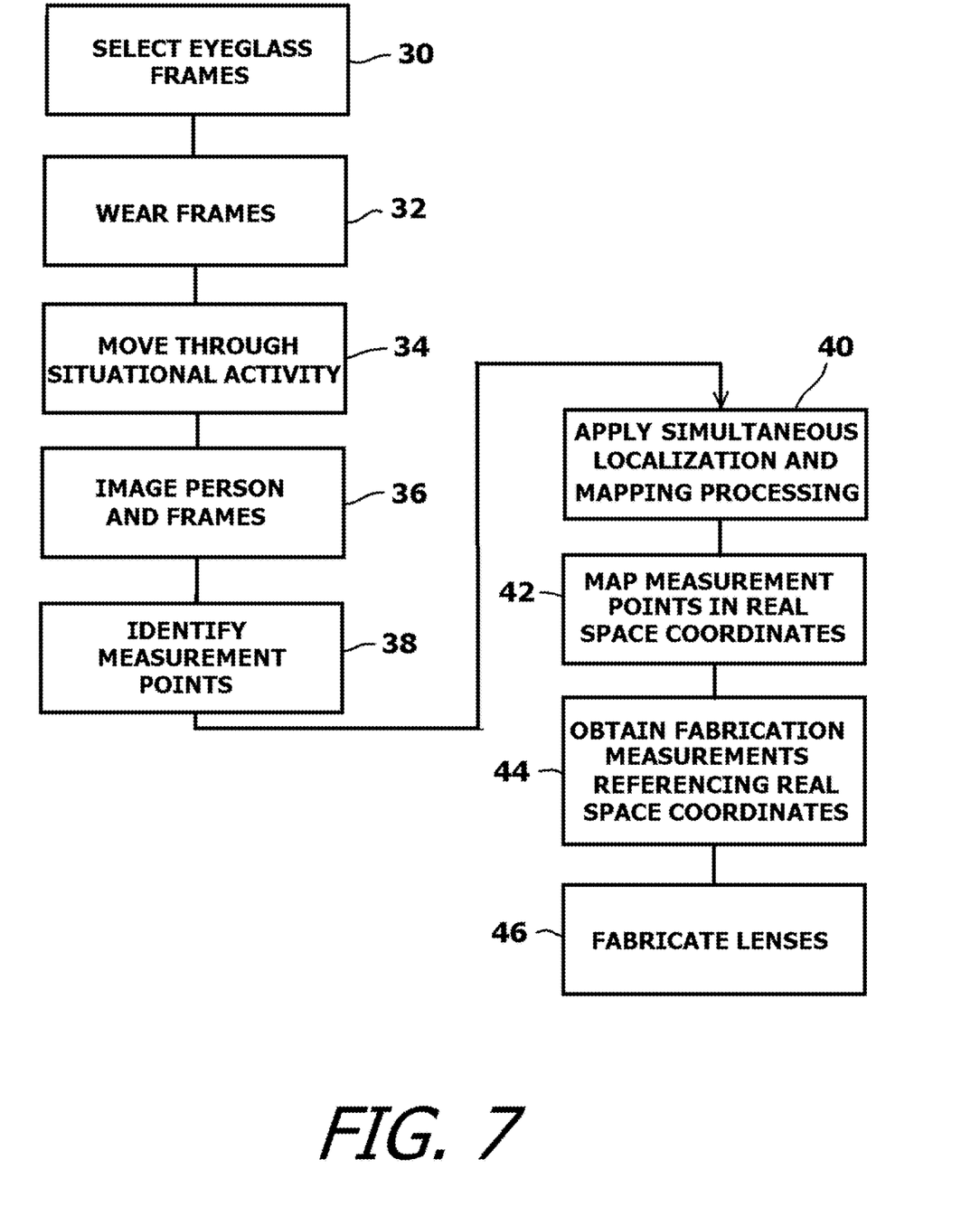
FIG. 7 is block diagram showing the methodology of the present invention system.

Referring to FIG. 7 in conjunction with FIG. 1, FIG. 5 and FIG. 6, the details of the operation of the present invention measurement system 10 is described. In order to utilize the measurement system 10, a set of eyeglass frames 20 is first selected. See Block 30. The person 18 is instructed to wear the eyeglass frames 12 in a comfortable manner. See Block 32. The person 18 is then asked to participate in a situational activity. See Block 34. For example, if the person 18 typically wears eyeglasses when sitting at a desk, the person 18 is asked to sit at a desk. If the person 18 typically wears eyeglasses when walking, the person 18 is asked to walk. Similar situational activities can be practiced for other common situations, such as standing, reading and like. What is of importance is that the person 18 wears the eyeglass frames 20 in the same manner as he/she would in real life. Likewise, the person 18 places his/her body in the same position and holds his/her head in the same manner as he/she would in everyday life. Accordingly, the overall pantoscopic tilt angle "PTA" is true to everyday life.

During the performance of the situational activities, the person 18 is imaged using the camera 14 on the smartphone 12. See Block 36. An optician, lens fabricator or other such technician can then identify measurement points 26 in at least two of the images 22 and preferably in a plurality of images. See Block 38. The measurement points 26 are the same as if the technician were taking physical measurements from the person 18 being imaged. The technician identifies measurement points 26 around the lens window 28 in the eyeglass frames 20. When the distance between these points are later calculated, the lens width "A" and the lens height "B" become known, as does the effective diameter "ED" of each prescription lens 24. The technician also identifies the geometric center "GC" of each prescription lens 24 in the images 22. The geometric centers "GC" are used to determine the datum line "DL" and the distance between the geometric centers can be determined along the datum line. Points on the eyeglass frames 20 are identified to calculate the frame length "L" between temples in the horizontal plane. Points on the eyeglass frames 20 are also used to calculate the bridge size, or distance between prescription lenses 24 "DBL". Using frame data points relative the vertical plane, the pantoscopic tilt angle "PTA" can be calculated. The proper pantoscopic tilt angle "PTA" for an individual is highly dependent upon the natural head posture of that person 18. This is because the vertical plane is a constant and any downward tilt of the head directly changes the tilt of the eyeglasses frames 20 relative the vertical plane. As such, the pantoscopic tilt angle "PTA" is the sum of the tilt angle T2 caused by the device panto plus the tilt angle T1 caused by head posture.

In the images 22, measurement points 26 on the face are also identified. The measurement points 26 that depend upon the anatomy of the person 18 wearing the eyeglass frames 24 include measure points 26 from which the pupil height "PH", pupil distance "PD", and rear vertex distance "RVD" can be measured. The pupil height "PH" is the measured height of the pupils above the bottom of the prescription lenses 24. The pupil distance "PD" is the distance between pupils in the horizontal plane. The rear vertex distance "RVD" is the gap distance between the pupil and the prescription lenses 24. The pantoscopic tilt angle "PTA", pupil height "PH" and the rear vertex distance "RVD" are measurements that depend upon how the prescription lens 24 are held in front of the eyes. They also depend upon how the person 18 normally orients his/her head when looking through the prescription lenses 24.

Once the measurement points 26 are identified in the images 22, two variables are known. That is, the position of the measurement points 26 in the images 22 and the distance between the measurement points 26 and the camera 14 that took the images 22. The position of the measurement points 26 is in the same scale as the images 22. The distance between the measurement points 26 and where the camera 14 was positioned is in real scale. With the measurement points 26 from the images 22 identified, the measurement points 26 are processed by the application software 16 being run in the smartphone 12. The measurement points 26 are subjected to simultaneous localization and mapping (SLAM) processing. See Block 40. SLAM processing tracks the identified measurement points 26 through successive camera frames and uses the known distance to the camera 14 in the images 22 to triangulate a three-dimensional coordinate position in real space for each identified measurement point 26. See Block 42. The three-dimensional coordinate positions are in real scale, having the same scale as the distance between the camera 14 and eyeglass frames 20 when the images 22 were taken. Once a coordinate position in real space is assigned to each measurement point 26, the application software 16 can quickly determine the distance between any two measurement points 26 in that coordinate system. Measurement points 26 can therefore be generated that correspond to the actual real scale distances or angles between any measurement points 26 or lines between measurement points 26. See Block 44. As a result, all the fabrication measurements presented in Table A can be obtained.

Once all the variables listed in Table A become known, proper prescription lenses 24 can be fabricated for the eyeglass frames 20. See Block 46. The prescription lenses 24 are not only properly crafted for magnification, but are customized for how the eyeglass frames 20 hold the lenses 14 in front of the user's eyes.

It will be understood that the exemplary embodiment of the present invention system that is illustrated and described is merely exemplary and that many aspects of the system can be redesigned in manners that are functionally equivalent. All such variations, modifications and alternate embodiments are intended to be included within the scope of the present invention as claimed.

What is claimed is:

1. A method of obtaining at least some measurements needed to correctly fabricate prescription lenses for a person without the use of imaging scales, said method comprising the steps of:
   providing eyeglass frames into which said prescription lenses are to be set;
   having the person wear said eyeglass frames without any auxiliary attachments;
   imaging the person wearing said eyeglass frames using a camera that has an autofocus function that is utilized to calculate image distances between the person wearing said eyeglass frames and said camera, wherein said camera is used from a first camera position and from at least one subsequent camera position, therein producing images having differing perspectives, wherein said image distances for said first camera position and said at least one subsequent camera position are measured in a first measurement scale;
   identifying common measurement points within at least some of said images, wherein at least some of said common measurement points undergo positional changes between said images having said differing perspectives;
   utilizing said positional changes in said common measurement points between at least some of said images and said image distances of first camera position and said at least one subsequent camera position to map three dimensional coordinates for said measurement points in said first measurement scale; and
   calculating fabrication measurements between said three dimensional coordinates in said first measurement scale; and
   fabricating said prescription lenses using said fabrication measurements.

2. The method according to claim 1, wherein said camera is a handheld electronic device that contains a processor and runs application software.

3. The method according to claim 1, wherein said common measurement points includes points on said eyeglass frames from which a lens length, a lens width, and a frame length can be directly measured.

4. The method according to claim 1, wherein said common measurement points include points on the person from which a pupil height and a pupil distance can be directly measured.

5. The method according to claim 1, wherein said common measurement points includes points on both said eyeglass frames and the person from which a pantoscopic tilt angle and rear vertex distance can be directly measured.

6. The method according to claim 2, wherein said application software running on said processor maps said three dimensional coordinates for said measurement points utilizing said positional changes in said common measurement points between at least some of said images and said image distances of said first camera position and said at least one subsequent camera position.

7. The method according to claim 2, wherein said application software running in said processor calculates fabrication measurements between said three dimensional coordinates in said first measurement scale.

8. A method of obtaining at least some measurements needed to correctly fabricate lenses for a person, said method comprising the steps of:
   providing eyeglass frames into which said lenses are to be set;
   providing a smartphone having a camera, an autofocus system, and a processor, wherein said processor runs application software that uses said autofocus system to measure camera distances between said camera and an object being imaged;
   imaging the person wearing said eyeglass frames from a first camera position and from at least one subsequent camera position, therein producing images having differing perspectives, wherein said first camera position and said at least one subsequent camera position are at said camera distances measured by said autofocus system, and wherein said camera distances are in a first measurement scale;
   utilizing said application software to identify common measurement points within at least some of said images, wherein at least some of said common measurement points undergo positional changes between said images having said differing perspectives;
   utilizing said application software to identify said positional changes in said common measurement points between at least some of said images and said camera distances of first camera position and said at least one subsequent camera position and to map three dimensional coordinates for said measurement points in said first measurement scale; and
   utilizing said application software to calculate fabrication measurements between said three dimensional coordinates in said first measurement scale.

9. The method according to claim 8, further including the step of fabricating said lenses using said fabrication measurements.

10. The method according to claim 8, wherein said fabrication measurements include measurements for pupil height, pantoscopic tilt angle, and rear vertex distance.

11. The method according to claim 8, wherein said common measurement points include points on said eyeglass frames from which a lens length, a lens width, and a frame length can be directly measured.

12. The method according to claim 11, wherein said common measurement points include points on the person from which a pupil height and a pupil distance can be directly measured.

13. The method according to claim 12, wherein said common measurement points include points on both said eyeglass frames and the person from which a pantoscopic tilt angle and rear vertex distance can be directly measured.

14. The method according to claim 8, wherein said application software running on said processor maps said three dimensional coordinates for said measurement points utilizing said positional changes in said common measurement points between at least some of said images and said camera distances of said first camera position and said at least one subsequent camera position.

15. The method according to claim 8, wherein said application software running on said processor calculates said fabrication measurements between said three dimensional coordinates in said first measurement scale.

16. A method of obtaining measurements needed to correctly fabricate prescription lenses, said method comprising the steps of:
   providing eyeglass frames into which said lenses are to be set;
   providing an electronic device having a camera, an autofocus system, and a processor, wherein said processor runs application software that uses said autofocus system to measure camera distances between said camera and an object being imaged;

imaging said eyeglass frames while being worn from a first camera position and from at least one subsequent camera position, therein producing images having differing perspectives, wherein said first camera position and said at least one subsequent camera position are at said camera distances measured by said autofocus system, and wherein said camera distances are in a first measurement scale;

identifying said common measurement points within at least some of said images utilizing said application software, wherein at least some of said common measurement points undergo positional changes between said images having said differing perspectives;

identifying said positional changes in said common measurement points between at least some of said images and said camera distances of said first camera position and said at least one subsequent camera position to map three dimensional coordinates for said measurement points in said first measurement scale; and calculating fabrication measurements between said three dimensional coordinates in said first measurement scale utilizing said application software.

17. The method according to claim 16, further including the step of fabricating said lenses using said fabrication measurements.

18. The method according to claim 16, wherein said fabrication measurements include measurements for pupil height, pantoscopic tilt angle, and rear vertex distance.

19. The method according to claim 16, wherein said common measurement points include points on said eyeglass frames from which a lens length, a lens width, and a frame length can be directly measured.

* * * * *